(12) United States Patent
Jacquamet et al.

(10) Patent No.: US 8,840,096 B2
(45) Date of Patent: Sep. 23, 2014

(54) DEVICE AND METHOD FOR HOLDING AND RELEASING A METALLIC SAMPLE HOLDER, AND USE OF THIS DEVICE

(75) Inventors: Lilian Jacquamet, Montferrat (FR); Catherine Izier, legal representative, Montferrat (FR); Hugo Stéphane Léon Jacquamet, legal representative, Montferrat (FR); Rémy Victor Stephen Jacquamet, legal representative, Montferrat (FR); Enzo Lilian Théo Jacquamet, legal representative, Montferrat (FR); Jean-Luc Ferrer, Corenc (FR)

(73) Assignees: Commissariat a l'Energie Atomique et aux Energies Alternatives, Paris (FR); Centre National de la Recherche Scientifique, Paris (FR)

( * ) Notice: Subject to any disclaimer, the term of this patent is extended or adjusted under 35 U.S.C. 154(b) by 934 days.

(21) Appl. No.: 13/000,872

(22) PCT Filed: Jul. 1, 2009

(86) PCT No.: PCT/IB2009/006610
§ 371 (c)(1),
(2), (4) Date: May 2, 2011

(87) PCT Pub. No.: WO2010/001260
PCT Pub. Date: Jan. 7, 2010

(65) Prior Publication Data
US 2012/0063571 A1 Mar. 15, 2012

(30) Foreign Application Priority Data
Jul. 1, 2008 (EP) .................................. 08290645

(51) Int. Cl.
*B25B 11/00* (2006.01)
*G01N 23/20* (2006.01)

(52) U.S. Cl.
CPC .............................. *G01N 23/20025* (2013.01)
USPC ................................ 269/8; 700/218; 378/208

(58) Field of Classification Search
CPC ...................................................... B25B 11/002
USPC ..................... 269/8, 53, 271; 378/208; 7/901; 700/218
See application file for complete search history.

(56) References Cited

U.S. PATENT DOCUMENTS 2,517,325 A * 8/1950 Lamb .............................. 600/11
2,671,484 A * 3/1954 Clark .............................. 81/451

(Continued)

FOREIGN PATENT DOCUMENTS

GB 970 104 A 9/1964

OTHER PUBLICATIONS

International Search Report and Written Opinion for PCT/IB2009/006610 dated Dec. 4, 2009.

(Continued)

*Primary Examiner* — Lee D Wilson
*Assistant Examiner* — Jamal Daniel
(74) *Attorney, Agent, or Firm* — Alston & Bird LLP (57) ABSTRACT

Device for holding and releasing a sample holder is provided. The device includes a support member having a pin with a magnet at its free end for holding the sample holder, tubular body mounted on the support member around and along the pin, and a tubular guide movably mounted inside the body and able to occupy a releasing position where its outer end surrounds the magnet, and a holding position where the guide is retracted inwards the body so that the magnet holds the sample holder. A cam on the guide cooperated with a cam follower-movably through the body upon movement of the guide and with elastic biasing the guide towards its releasing position, to reversibly lock the follower in the holding position when the guide is moved inwards toward the body and to retrieve the initial releasing position, after further moving the guide inwards and releasing this movement.

16 Claims, 4 Drawing Sheets

(56) References Cited

U.S. PATENT DOCUMENTS

| | | | |
|---|---|---|---|
| 3,478,207 A | 11/1969 | Goerke et al. | |
| 3,700,250 A * | 10/1972 | Bautz | 279/35 |
| 6,260,980 B1 * | 7/2001 | Ping | 362/120 |
| 8,162,363 B2 * | 4/2012 | Wang | 294/65.5 |
| 2002/0126802 A1 * | 9/2002 | Olson et al. | 378/208 |
| 2004/0164571 A1 | 8/2004 | Pedrazzini | |
| 2007/0228049 A1 | 10/2007 | Nordmeyer et al. | |
| 2010/0318217 A1 * | 12/2010 | Ferrer et al. | 700/218 |
| 2012/0063571 A1 * | 3/2012 | Jacquamet et al. | 378/208 |
| 2012/0296469 A1 * | 11/2012 | Yoshinaga et al. | 700/218 |
| 2013/0341845 A1 * | 12/2013 | Zanella et al. | 269/8 |

OTHER PUBLICATIONS

Ohana, J. et al., *CATS: A Cryogenic Automated Transfer System Installed on the Beamline FIP at ESRF*, J. Appl. Cryst. 37, (2004), pp. 72-77.

Snell, G. et al., *Automated Sample Mounting and Alignment System for Biological Crystallography at a Synchrotron Source*, Structure, vol. 12, (2004), pp. 537-545.

* cited by examiner

DEVICE AND METHOD FOR HOLDING AND RELEASING A METALLIC SAMPLE HOLDER, AND USE OF THIS DEVICE

FIELD OF THE INVENTION

The present invention relates to a device and method for alternately holding and releasing a metallic sample holder, such as a metallic cap closing a sample containing vial. The invention also concerns the use of such a device for example to transfer or maintain the sample to or in an analysis location, to a location for the preparation of the sample, to a location with a cold freezing medium or to/from a location where the atmospheric humidity is controlled for the sample. The invention particularly applies to the manipulation of macromolecular crystal samples, such as protein crystals, for X-ray crystallography measurements.

BACKGROUND OF THE INVENTION

Solving the structure of biological macromolecules has become an important phase in the understanding of biological mechanisms at the molecular level. This structural information can be used to manipulate proteins for industrial applications, such as catalysis, and is also often used as the first step towards the design of active molecules that will give birth to new medications (as an example, mention can be made of inhibitors of the HIV enzymes).

Among the different techniques available, X-ray crystallography is a widely used technique for providing a three-dimensional representation of macromolecules. An X-ray crystallography experiment generally consists in placing the macromolecule to be studied—usually a protein—in an intense X-ray beam, thus producing an image of the diffracted X-rays, the intensity thereof being then recorded by the means of a specific detector. From these data, the 3-D distribution of the electronic density of the studied macromolecule can be obtained, from which the 3-D structure of the studied molecule may be built.

Most currently used sample containers for macromolecule crystals include a sample that is mounted on a metallic sample holder closing a vial. Such containers each comprise a metallic base or cap, in which a pin is inserted. A loop, which is glued at the tip of this pin, supports the crystal sample, whose size is largely less than 1 mm and typically of about 10 µm to 300 µm. During transportation, the vial is thus closed by the cap of the metallic holder. This way, the sample is stored in the liquid nitrogen contained in the vial.

Due to the intensity of the X-ray beam, it is usually necessary to maintain the sample at a temperature close to that of liquid nitrogen. Thus, the crystal—typically an object of a dimension largely inferior to one millimeter—is to be placed a short time after its obtaining in a Dewar container full of to liquid nitrogen, and maintained under that condition during its transportation. Throughout data recording, the sample, placed on a goniometer, is constantly bathed in a flow of nitrogen gas at a temperature of about 100 K. During its transfer from the Dewar to the goniometer, the crystal must never be exposed to the ambient atmosphere, and must at all times be maintained at a temperature of no more than 130 K. This operation, when realized manually, is a very slow and delicate step of the process. Now, fully automated transfer systems exist, but each new system has to prove a very high degree of reliability before being accepted by the research community. Indeed, a sample sometimes has taken months to produce. The risk of spoiling it is generally considered to be too high to try anything else but what is already known as working with a reasonable rate of failure.

In order to answer the increasing demand in solving protein structure from the structural genomics projects as well as from pharmaceutical industry, the automation of the beamlines dedicated to protein crystallography has become a necessity. The sample mounting/dismounting on a goniometer is an important step in the automation processes and therefore important developments have been performed. The goniometer is the device which rotates the sample in order to record the diffraction pattern leading to the 3D structure of the protein. Several automated sample changers have been developed throughout the world, such as the system "CATS" (see Ohana J., Jacquamet L., Joly J., Bertoni A., Taunier P., Michel L., Charrault P., Pirocchi M., Carpentier P., Borel F., Kahn R., Ferrer J-L.: CATS: a Cryogenic Automated Transfer System installed on the beamline FIP at ESRF. J Appl Cryst 2004, 37:72-77), whose capabilities of the main core—a 6-axis robot from the Staubli Company—have been extended to another system named "G-Rob". This last system also offers the possibility to record diffraction data, being a goniometer-robot that combines the two functions of the robotic sample changer and of the data recording without the transfer on the goniometer.

For "CATS" systems as well as for all other sample changers, the weakness in the mounting/dismounting processes is the sample transfer from the storage location (a liquid nitrogen Dewar) to the magnet allowing the sample to hold tight during the data collection. It is also noteworthy that this problem is even more general since it is also present in the manual transfer on the magnet of a laboratory X-ray source. The difficulty and weakness thus reside in the transfer of the sample from the Dewar to the sample holder. Since the sample cap is metallic, the mounting process is easy to make. The problem arises when the robot wants to retrieve the sample after X-ray exposures. The vial is equipped with a ring to hold the metallic cap. However, since the sample holder magnet is stronger than that of the vial magnetic ring, the robot can not retrieve the sample by pulling the vial, and the sample dismounting becomes an issue.

To solve this problem, different solutions have been carried out, all using pneumatic or electric external devices equipping the sample holder (see for instance G. Snell, C. Cork, R. Nordmeyer, E. Cornell, G. Meigs, D. Yegian, J. Jaklevic, J. Jin, R. Stevens, and T. Earnest, Automated Sample Mounting and Alignment System for Biological Crystallography at a Synchrotron Source. Structure, 2004, 12: 537-45).

The major drawbacks of all these solutions with such external devices are their non-reliability and complexity.

SUMMARY OF THE INVENTION

One purpose of the present invention is to provide a device for alternately holding and releasing a metallic sample holder, such as a metallic cap closing a sample containing vial, which remedies these drawbacks, the device comprising:
  a support member,
  a pin which is fastened to the support member and which is provided at its free end with a magnet for holding said sample holder, and
  an outer fixed tubular body which is mounted on said support member around and substantially along said pin.

For this purpose, the device according to the invention is characterized in that it further comprises:
  an inner tubular guide which is movably mounted along an axis inside said body and is able to occupy an axially outer releasing position of the sample holder where its axially outer end surrounds said magnet, and an axially inner holding position of the sample holder where the guide is retracted axially inwards said body so that said magnet may hold the sample holder, at least one cam having a curved track being formed on said guide and cooperating with a follower which is included in the device and which is movably mounted through said body and able to follow said track upon movement of the guide, and elastic means which surround said pin and which bear against said support member and against an axially inner end of the guide to bias the latter towards its releasing position, said at least one cam cooperating with said elastic means to reversibly lock said or each follower in said holding position when the guide is moved inwards said body, and to retrieve said initial releasing position after further moving the guide inwards to unlock the follower and then releasing this inward movement.

By "tubular", it is meant in instant description that both body and guide may generally have either a cylindrical or prismatic form (e.g. either a circular or square section, respectively).

By "axially", reference is made in instant description to a direction which is parallel to that of said axis of movement of the guide, e.g. parallel to a translation axis.

According to another feature of the invention, the device may be an integral part of a sample manipulator system being for example adapted to transfer by means of said magnet the sample from a storing location to an analysis location, such as an X-ray beam. Alternatively, this manipulator system may be adapted by means of said magnet to maintain the sample in this analysis location, the device being then part of a goniometer. Still alternatively, this manipulator system may be adapted to transfer the sample to a location aimed at its preparation under specific conditions (e.g. its temperature, humidity or any other physical parameter), to a cold freezing location, or to/from a location where the atmospheric humidity is specifically controlled for the sample.

It will be noted that this device provides the ability to easily mount/dismount the metallic vial cap on/from the sample manipulator system, without the use of any external pneumatic or electric means used in the prior art. This functionality fully answers the European standard for sample changers, as defined in the "SPINE" European project. The inventive device thus significantly increases the reliability and simplicity of the transfer, as compared to prior art systems using theses external means, which is crucial for all "high throughput" applications.

The inventive device, which does not need any electric or pneumatic control, is thus perfectly suitable for the adaptation of sample changers, like "CATS" or other ones, to classical goniometer heads. This inventive device can also be part of a robot-goniometer, as the "G-Rob" system.

According to another feature of the invention, said guide may be at least slidably mounted on an inner face of said body upon pushing inwards said outer end of the guide, said elastic means comprising a compression spring mounted between said pin and said body.

Advantageously, a plurality of identical cams—preferably two diametrically opposite cams—which are respectively provided with said followers may be formed on said guide, so that said followers move at the same time in their respective tracks from said holding position to said releasing position, and vice versa.

Also advantageously, said at least one cam may be a cardioid cam, said or each follower, such as a bolt, being able to occupy a plurality of discrete stages along said track which is substantially heart-shaped into the wall of said guide with an axially inner point and two axially outer lobes, these stages comprising a holding stage corresponding to said holding position where said or each follower is locked substantially between said lobes, and a releasing stage corresponding to said releasing position where said or each follower is locked at said inner point.

Also preferably, said body may be provided with translation guiding means, which are designed to cooperate with a sliding element of said guide to form at least one guideway for the guide. These translation guiding means may comprise at least one notch which is formed at the axially outer end of said body and which is adapted to receive a corresponding protruding sliding nut forming said sliding element, this nut protruding in a direction perpendicular to said axis of movement of the guide.

According to a preferred embodiment of the invention, the device may further comprise a casing which is rotatably mounted on said support member and which at least partially surrounds said body, this casing being provided at its axially outer end with said at least one follower which protrudes inwards and is guided perpendicularly to said axis across a through arcuate hole formed in the wall of the body in front of said track so that said or each follower remains on the latter, this casing being rotatably movable relative to said body due to the displacement of said or each follower across said hole in response to the movement of said guide.

Still according to this embodiment, said casing may comprise several diametrically opposite cover members whose respective ends are provided with said corresponding followers, and which are connected together by symmetrical recesses of the casing.

According to another aspect of the invention, the device is provided with said sample holder which is of metallic holder type, such as a cap-closed vial, said cap having an outer diameter that is greater than the inner diameter of the outer end of said guide, so that the cap may make this guide retract upon its movement inwards the body. Advantageously, said cap-closed vial may contain said sample in liquid nitrogen at a temperature less than or equal to 130 K, preferably less than or equal to 100 K, the sample being a macromolecule crystal such as a protein crystal, a longitudinal pin being inserted in an inner face of said cap, said pin having at its free end a tip to which a loop supporting said sample is adhered.

A method according to the invention for alternately holding and releasing a metallic sample holder, in particular a metallic cap closing a sample containing vial to be transferred or maintained to or in an analysis location, to a location for the preparation of the sample, to a location with a cold freezing medium or to/from a location where the atmospheric humidity is controlled for the sample, is implemented by the inventive device as described above, and this method comprises, for making said magnet hold the sample holder in a locked holding position:

a) placing the sample holder in contact with the outer end of said guide, then b) moving the sample holder—guide assembly inwards said body along said axis, so as to retract the guide axially inside the magnet and to lock said or each follower in a holding stage formed in the track of said at least one cam, and this method comprises, for releasing the sample holder from the magnet in said releasing position:

c) further moving the sample holder—guide assembly axially inwards said body, so as to unlock said or each follower from its holding stage in its track, and then d) releasing this inward movement, so that said or each follower retrieves an initial releasing stage in its track and the guide retrieves its initial axially outer releasing position where its outer end surrounds the magnet, which makes the sample holder be distant enough from this magnet.

Preferably, steps b) and c) each comprise pushing the sample holder—guide assembly axially inwards said body along said axis, while guiding this guide in translation along at least one guideway of the body. Guiding in translation said guide makes said at least one follower move in a first circumferential direction across a through arcuate guiding hole that may be formed in the wall of the body in front of said track, according to said preferred embodiment, which movement makes a casing of the body ending with said at least one follower rotate in said first direction on said support member.

Still according to this embodiment, step d) makes said at least one follower move in said guiding hole and said casing rotate on said support member in a second circumferential direction opposite said first direction, upon releasing the inward movement of said guide, so that the latter retrieves its initial axially outer releasing position.

BRIEF DESCRIPTION OF THE DRAWINGS

The above-mentioned characteristics of the present invention, along with others, will be understood more clearly on reading the following description of several examples of the invention, which are given for illustrative purposes and are not intended to limit the invention, said description referring to the attached drawings, wherein.

DETAILED DESCRIPTION OF THE INVENTION

Figure 1:
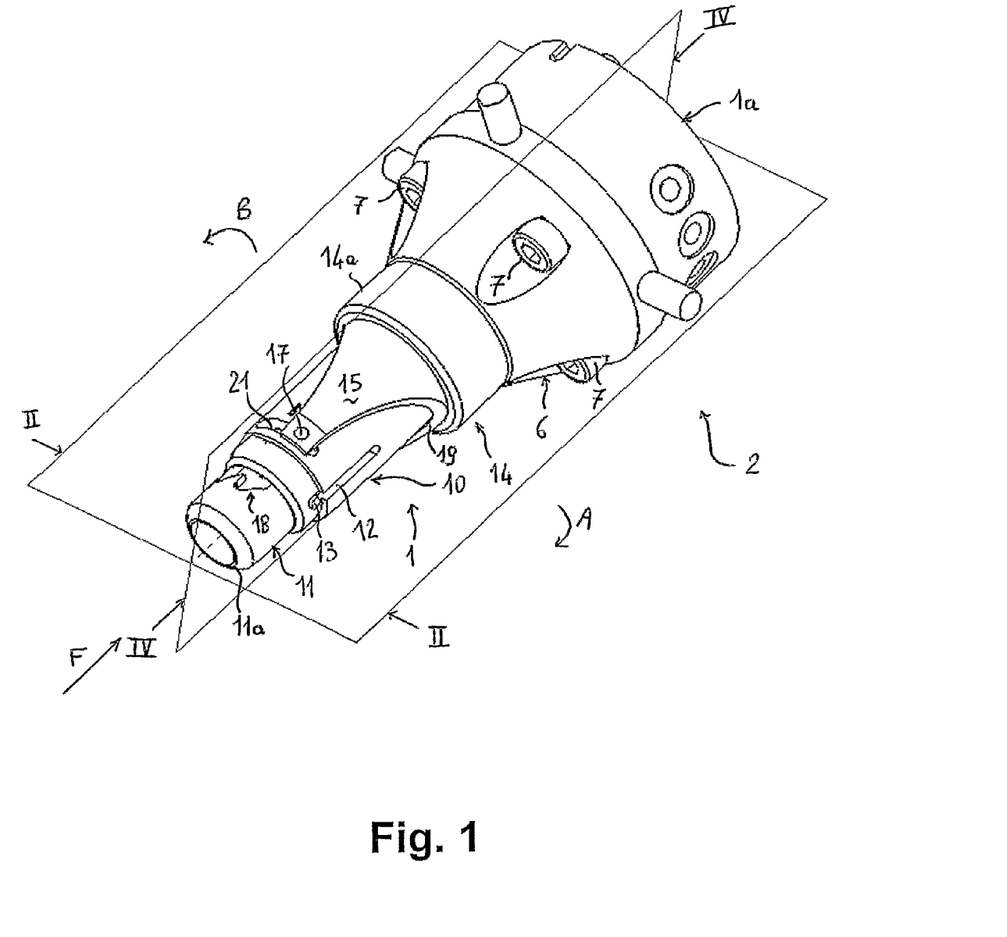
FIG. 1 is a perspective view of a manipulator tool integrating a device according to the invention for holding/releasing a metallic vial cap, shown in a releasing position of this cap.
Figures 2, 3:
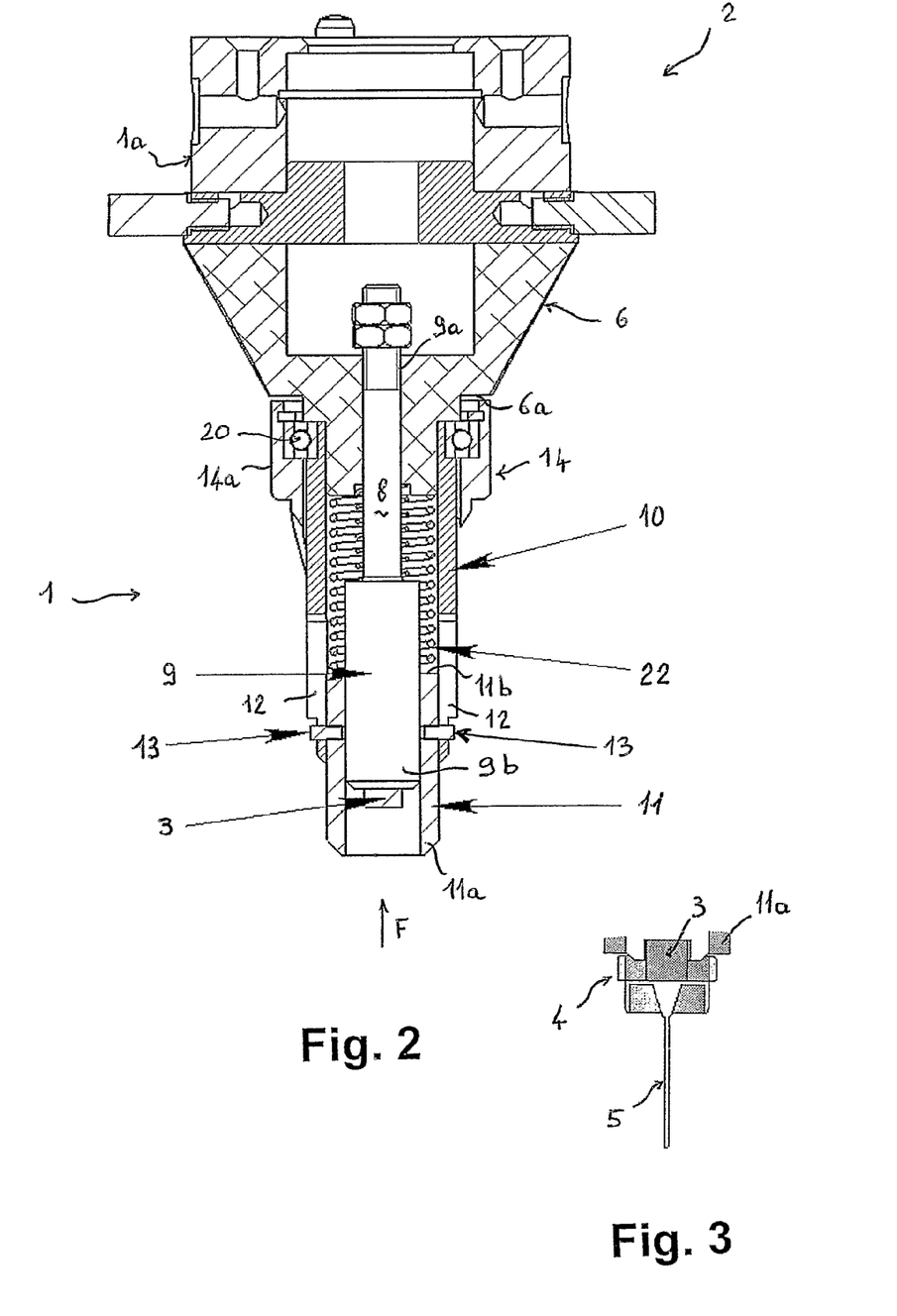
FIG. 2 is an axial median sectional view along plane II-II of FIG. 1 of the inventive device shown therein.
FIG. 3 is a diagrammatic axial sectional view of a part of the outer end of the device shown in FIG. 2 and holding this cap.
Figure 4:
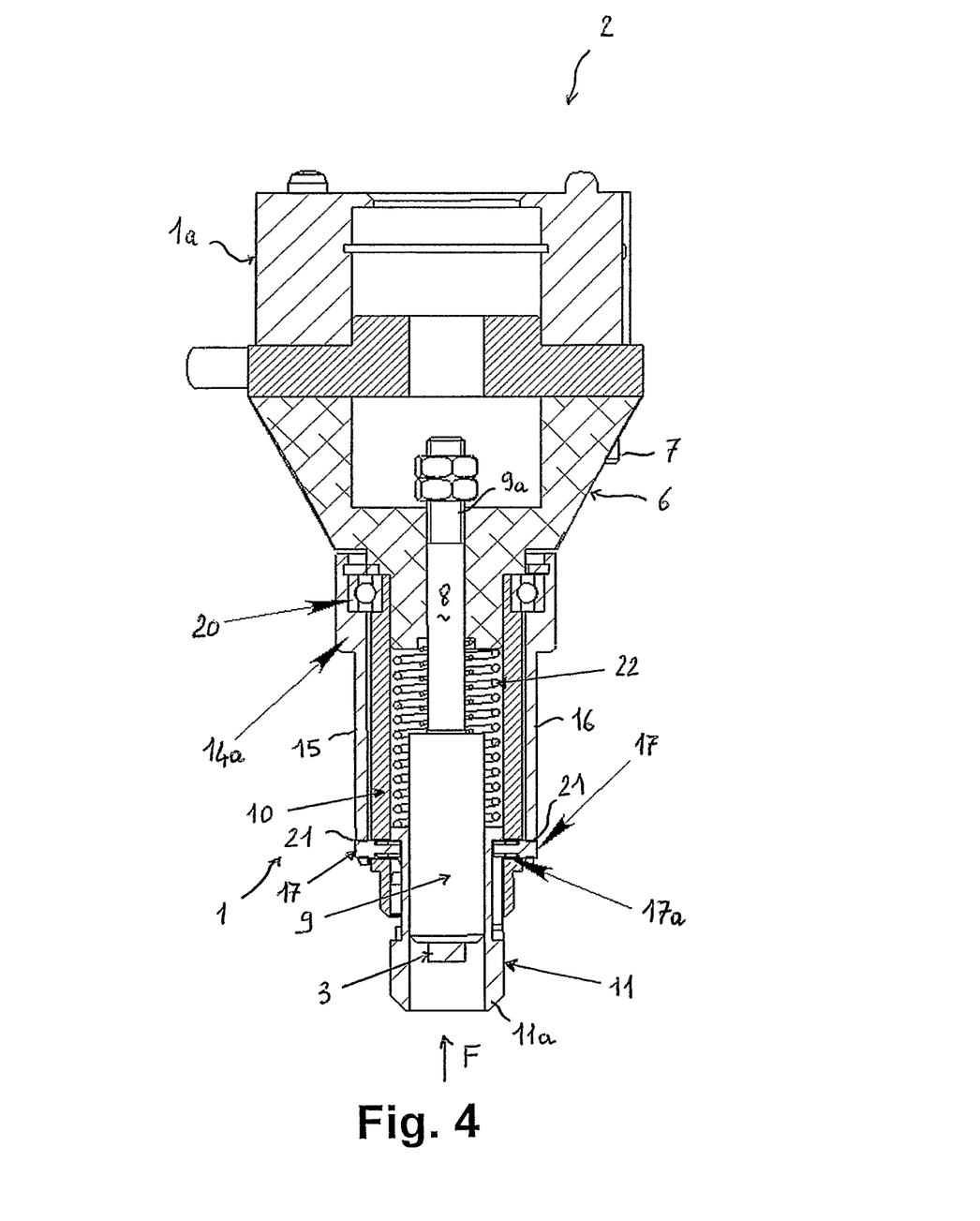
FIG. 4 is an axial median sectional view along plane IV-IV of FIG. 1 of this device, plane IV-IV being perpendicular to plane II-II.

The device 1 shown in FIGS. 1, 2 and 4 is an integral part of a sample manipulator system 2 to which it is attached by means of a tool changer 1a. The device 1 is for example designed to transfer and/or maintain a sample by means of a magnet 3 included in this device 1, to and/or in an analysis location such as an X-ray beam. The sample can be a protein crystal stored in a closed vial containing a macromolecule crystal in liquid nitrogen at a temperature of preferably less than or equal to 100 K. This device 1 is designed to alternately hold and release a metallic cap 4 closing the vial thanks to the magnet 3, which cap 4 is shown in FIG. 3 and is of metallic holder type. The cap 4 is equipped on its inner face with a longitudinal pin 5 having at its free end a tip (non illustrated) to which a loop supporting the crystal is adhered.

This exemplary device 1 comprises:
a tapered support member 6 which is fastened to the tool changer 1a by appropriate means, such as fixing bolts 7, and which is provided with an axial bore 8;
a pin 9 which is accommodated inside the bore 8 and which comprises a first end 9a bolted in the support member 6 and a second end 9b provided with the magnet 3;
an outer fixed tubular body 10 which is coaxially mounted on the support member 6 around and along the pin 9;
an inner tubular guide 11 which is reversibly slidably mounted on an inner face of the body 10 via two diametrically opposite axial notches 12 respectively cooperating in translation with two radially protruding nuts 13 of the guide 11 so as to form a guideway for the latter, which guide 11 is able to occupy an axially outer releasing position (shown in FIGS. 1, 2 and 4) of the cap 4 where its outer end 11a radially surrounds the magnet 3, and an axially inner holding position of the cap 4 where the guide 11 is retracted axially inwards the body 10 so that the magnet 3 may hold the cap 4; and
a casing 14 partially surrounding the body 10 and comprising a cylindrical basis 14a rotatably mounted via a ball bearing 20 on a shoulder 6a of the support member 6 and two diametrically opposite cover members 15, 16 (which form an integral single piece) extending from this basis 14a and connected together by two symmetrical recesses 19, which cover members 15, 16 each have an isosceles curved triangle shape whose axially outer summit is provided with a moving bolt forming a follower 17 able to follow the track 18a of a corresponding cam 18 formed on the guide 11, the casing 14 being rotatably movable relative to the body 10 in response to the sliding of the guide 11.

As visible in FIG. 3 and as hereunder explained, the cap 4 has an outer diameter greater than the inner diameter of the outer end 11a of the guide 11, being thus able to make the guide 11 retract upon its movement inwards the body 10.

Figure 5:
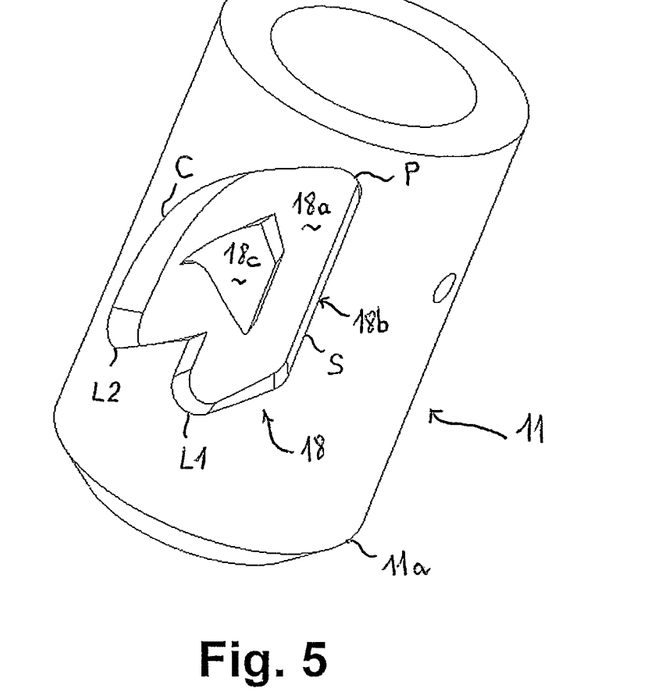
FIG. 5 is a perspective view of the outer part of the guide of the device as shown in FIG. 1.
Figure 6:
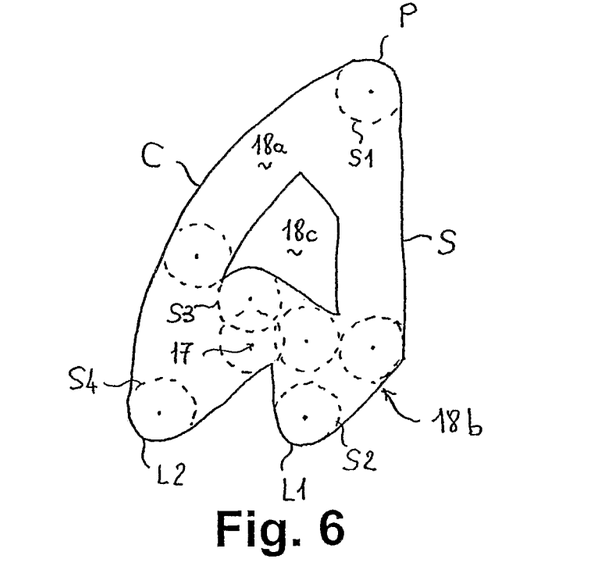
FIG. 6 is a diagrammatic elevation view showing in dotted lines a plurality of stages successively occupied by a follower moving along the track of the cardioid cam of the guide, as shown in FIG. 5.

According to the invention, both diametrically opposed symmetrical cams 18, each defining a cardioid track 18a (see FIG. 5), are formed on the cylindrical wall of the guide 11 and respectively cooperate with both radial followers 17 which are movably and simultaneously guided in both circumferential directions A and B on their respective tracks 18a across respective symmetric arcuate through guiding holes 21 formed in the wall of the body 10 radially above the tracks 18a, so as to make the cover members 15 and 16 rotate around the body 10 due to the displacement of both followers 17 in their respective guiding holes 21 in response to the translational movement of the guide 11. The cams 18 cooperate with a helical compression spring 22 coaxially surrounding the pin 9, which is accommodated inside the body 10 and which elastically bears against the support member 6 and an inner end 11b of the guide 11 so as to bias the latter towards its releasing position. The heart-shaped cams 18 and the spring 22 are designed to:

lock each follower 17 in the holding position (corresponding to a holding stage S3 of the followers 17 where each of them is locked between the two lobes L1 and L2 of its cam track 18a, see FIGS. 5 and 6) when the guide 11 is pushed inwards the body 10, and to retrieve the initial releasing position (corresponding to a releasing stage S1 of the followers 17 where each of them is locked at an inner axial point P or summit of the cardioid curve 18b, see again FIGS. 5 and 6), after further pushing the guide 11 inwards to unlock each follower 17 and then releasing this inward pushing.

More precisely and as visible in FIG. 4, both bolt followers 17 are preferably provided with rolls 17a, so as to minimize friction and maximize rolling of these bolts 17 along their respective cardioid tracks 18a, which are each defined by a pathway between the outer cardioid curve 18b and a central inner block 18c.

The method for holding the cap 4 via the magnet 3 in the locked holding position S3 may be implemented by means of this inventive device 1 in the following way.

the cap 4 closing the vial is placed in contact with the outer end 11a of the guide 11, then the vial-cap-guide assembly is pushed axially inwards the body 10 (either by a robot or by a human operator, see arrow F for this pushing force in FIGS. 1, 2 and 4) while guiding the guide 11 in translation along the notches 12 of the body 10, so as to retract the guide 11 axially inside the magnet 3 and to lock each follower 17 in the holding stage S3 formed in its cam track 18a, this holding stage S3 being obtained by the movement of each follower 17 in a first circumferential direction A in the corresponding arcuate guiding hole 21 and the resulting concomitant rotation of the cover members 15 and 16 in this direction A.

Conversely, the method for releasing this cap 4 from the magnet 3 in the releasing position may be implemented in the following way:

the vial-cap-guide assembly is further pushed axially inwards the body 10 (either by a robot or by a human operator) while guiding the guide 11 in translation along the notches 12 of the body 10, so as to unlock each follower 17 from its holding stage S3 in its track 18a due to the further movement of each follower 17 in this first direction A in the corresponding guiding hole 21, and then this inward movement is released (i.e. stopped), so that each follower 17 retrieves the initial releasing stage S1 through its guiding hole 21 in its track 18a and the guide 11 retrieves its initial axially outer releasing position where its outer end 11a radially surrounds the magnet 3, via a rotation of the cover members 15 and 16 in a second circumferential direction B opposite said first direction A, which makes the cap 4 be distant enough from the magnet 3.

As visible in FIG. 6, four main discrete or separate stages S1 to S4 for each bolt follower 17 may be distinguished in each cardioid cam track 18a:

in the first above-referred releasing stage S1, each follower 17 is locked in the axially inner point P of the cardioid curve 18b;

in a second intermediary stage S2 due to the rotation in the first direction A of each follower 17 in its guiding hole 21 and of the cover members 15 and 16 on the support member 6 and around the body 10, following to said inwards pushing of the guide 11, each follower 17 is located at the axially outer bottom of one of the lobes L1 (this lobe L1 being connected to the point P of the cardioid curve 18b by a substantially straight axial segment S);

in the third above-referred holding stage S3 which is the final consequence of this inwards pushing of the guide 11, each follower 17 leaves this second stage S2 to be locked substantially between both lobes L1 and L2 and against the inner block 18c of the corresponding cam 18; and in the fourth intermediary stage S4 due to the further inwards pushing of the guide 11, each follower 17 leaves this third holding stage S3 to be located at the axially outer bottom of the other lobe L2 (this lobe L2 is connected to the point P of the cardioid curve 18b by a continuously curved line C).

As mentioned above, the transition for each follower 17 from that fourth stage S4 to the first releasing stage S1 is due to the releasing of the pushing force F applied to the vial-cap-guide assembly, which makes both followers 17 and cover members 15 and 16 rotate in said second opposite direction B while the guide 11 slides axially outwards the body 10.

In order to ensure a smooth operation of the inventive device 1, it will be noted that:

each cam track 18a with its different curves C, L1, L2 and slopes S has been specially designed, so that the bolt followers 17 move straight from point to point without any jamming in particular stages S1 to S4;

the strength of the magnet 3 has been chosen to ensure a smooth mechanism and also to block the magnet 3 and the cap 4 at a fixed position (the spring 22 having also the function to compensate the mechanical plays); and that the materials of the cams 18 and followers 17 are such to impart a satisfactory longevity to the device 1.

The invention claimed is:

1. Device for alternately holding and releasing a metallic sample holder, in particular a metallic cap closing a sample containing vial, the device comprising:

a support member, a pin fastened to the support member and provided at its free end with a magnet for holding the sample holder, and an outer fixed tubular body which is mounted on said support member around and substantially along said pin, characterized in that the device further comprises:

an inner tubular guide which is movably mounted along an axis inside said body and is able to occupy an axially outer releasing position of the sample holder where its axially outer end surrounds said magnet, and an axially inner holding position of the sample holder where the guide is retracted axially inwards said body so that said magnet may hold the sample holder, at least one cam having a curved track being formed on said guide and cooperating with a follower which is included in the device and which is movably mounted through said body and able to follow said track upon movement of the guide, and elastic means which surround said pin and which bear against said support member and against an axially inner end of the guide to bias the latter towards its releasing position, said at least one cam cooperating with said elastic means to reversibly lock said or each follower in said holding position when the guide is moved inwards said body, and to retrieve said initial releasing position after further moving the guide inwards to unlock the follower and then releasing this inward movement.

2. Device according to claim 1, wherein said guide is at least slidably mounted on an inner face of said body upon pushing inwards said outer end of the guide, said elastic means comprising a compression spring mounted between said pin and said body.

3. Device according to claim 1, wherein a plurality of identical cams which are respectively provided with said followers are formed on said guide, so that said followers move at the same time in their respective tracks from said holding position to said releasing position, and vice versa.

4. Device according to claim 1, wherein said at least one cam is a cardioid cam, said or each follower, such as a bolt, being able to occupy a plurality of discrete stages along said track which is substantially heart-shaped into the wall of said guide with an axially inner point and two axially outer lobes, this stages comprising a holding stage corresponding to said holding position where said or each follower is locked substantially between said lobes, and a releasing stage corresponding to said releasing position where said or each follower is locked at said inner point.

5. Device according to claim 1, wherein said body is provided with translation guiding means, which are designed to cooperate with a sliding element of said guide to form at least one guideway for the guide.

6. Device according to claim 5, wherein said translation guiding means comprise at least one notch which is formed at the axially outer end of said body and which is adapted to receive a corresponding protruding sliding nut forming said sliding element, this nut protruding in a direction perpendicular to said axis of movement of the guide.

7. Device according to claim 1, wherein it further comprises a casing which is rotatably mounted on said support member and which at least partially surrounds said body, this casing being provided at its axially outer end with said at least one follower which protrudes inwards and is guided perpendicularly to said axis in a through arcuate hole formed in the wall of the body in front of said track so that said or each follower remains on the latter, this casing being rotatably movable relative to said body due to the displacement of said or each follower in said hole in response to the movement of said guide.

8. Device according to claim 3, wherein said casing comprises several diametrically opposite cover members whose respective ends are provided with said corresponding followers, and which are connected together by symmetrical recesses of the casing.

9. Device according to claim 1, wherein it is an integral part of a sample manipulator system which, by means of said magnet, is for example adapted to:
   transfer the sample from a storing location to an analysis location, or to a location for the preparation of the sample under specific physical parameters,
   maintain the sample in this analysis location consisting of an X-ray beam, this device then being part of a goniometer,
   transfer the sample in order to freeze it in a cold medium, such as liquid nitrogen, or to
   transfer the sample to or from a location where the atmospheric humidity is specifically controlled for the sample.

10. Device according to claim 9, wherein it is provided with said cap-closed vial which is of metallic holder type, said cap having an outer diameter that is greater than the inner diameter of the outer end of said guide, so that the cap may make this guide retract upon its movement inwards the body.

11. Device according to claim 9, wherein said cap-closed vial contains said sample in liquid nitrogen at a temperature less than or equal to 130 K, preferably less than or equal to 100 K, the sample being a macromolecule crystal such as a protein crystal, a longitudinal pin being inserted in an inner face of said cap, said pin having at its free end a tip to which a loop supporting said sample is adhered.

12. Method for alternately holding and releasing a metallic sample holder, in particular a metallic cap closing a sample containing vial to be transferred or maintained to or in an analysis location, to a location for the preparation of the sample, to a location with a cold freezing medium or to/from a location where the atmospheric humidity is controlled for the sample, the method being implemented by a device according to claim 1, characterized in that this method comprises, for making said magnet hold the sample holder in a locked holding position:
   a) placing the sample holder in contact with the outer end of said guide, then
   b) moving the sample holder-guide assembly inwards said body along said axis, so as to retract the guide axially inside the magnet and to lock said or each follower in a holding stage formed in the track of said at least one cam,
   and in that this method comprises, for releasing the sample holder from the magnet in said releasing position:
   c) further moving the sample holder-guide assembly axially inwards said body, so as to unlock said or each follower from its holding stage in its track, and then
   d) releasing this inward movement, so that said or each follower retrieves an initial releasing stage in its track and the guide retrieves its initial axially outer releasing position where its outer end surrounds the magnet, which makes the sample holder be distant enough from this magnet.

13. Method according to claim 12, wherein steps b) and c) each comprise pushing the sample holder-guide assembly inwards said body along said axis while guiding this guide in translation along at least one guideway of the body.

14. Method according to claim 13, wherein guiding in translation said guide makes said at least one follower move in a first circumferential direction (A) in a through arcuate guiding hole formed in the wall of the body in front of said track, which movement makes a casing of the body ending with said at least one follower rotate in said first direction on said support member.

15. Method according to claim 14, wherein step d) makes said at least one follower move in said guiding hole and said casing rotate on said support member in a second circumferential direction (B) opposite said first direction (A), upon releasing the inward movement of said guide, so that the latter retrieves its initial axially outer releasing position.

16. Use of a device according to claim 1, the device being an integral part of a sample manipulator system, to:
   transfer the sample or to maintain it respectively to or in an analysis location,
   transfer the sample to a location designed for its preparation,
   transfer the sample to a location with a cold freezing medium, such as liquid nitrogen, and/or
   transfer the sample to or from a location where the atmospheric humidity is specifically controlled.

* * * * *